United States Patent
Kelly et al.

(10) Patent No.: US 9,642,952 B1
(45) Date of Patent: May 9, 2017

(54) TWO STAGE COLOSTRUM COLLECTION SYSTEM

(71) Applicants: Patricia A. Kelly, Burbank, CA (US); Joan P. Ortiz, Burbank, CA (US); Brian Carletta, Burbank, CA (US)

(72) Inventors: Patricia A. Kelly, Burbank, CA (US); Joan P. Ortiz, Burbank, CA (US); Brian Carletta, Burbank, CA (US)

(73) Assignee: LIMERICK, INC., Burbank, CA (US)

( * ) Notice: Subject to any disclaimer, the term of this patent is extended or adjusted under 35 U.S.C. 154(b) by 0 days.

(21) Appl. No.: 15/082,974

(22) Filed: Mar. 28, 2016

(51) Int. Cl.
*A61M 1/00* (2006.01)

(52) U.S. Cl.
CPC .................. *A61M 1/0066* (2013.01)

(58) Field of Classification Search
CPC .... A61M 1/0066; A61M 1/06; A61M 1/0072; A61M 1/0074; A61M 5/3135; A61M 5/178; A61M 2005/2073; A61M 5/315
See application file for complete search history.

(56) References Cited

U.S. PATENT DOCUMENTS

| | | | |
|---|---|---|---|
| 213,014 A | | 3/1879 | Von Beust. |
| 684,078 A | | 10/1901 | Martin |
| 2,419,795 A | | 7/1945 | Saunders |
| 4,857,051 A | * | 8/1989 | Larsson .................. A61M 1/06 604/346 |
| 6,652,484 B1 | | 11/2003 | Hunckler et al. |
| 8,979,819 B2 | | 3/2015 | Sherman |
| 8,998,879 B2 | | 4/2015 | Sherman et al. |
| 2008/0045887 A1 | * | 2/2008 | Larsson .................. A61M 1/06 604/74 |
| 2012/0289936 A1 | | 11/2012 | Ingram et al. |
| 2013/0030379 A1 | | 1/2013 | Ingram et al. |
| 2013/0281983 A1 | | 10/2013 | Sherman |
| 2013/0296779 A1 | * | 11/2013 | Kuehne ............... A61M 5/3134 604/93.01 |
| 2014/0052106 A1 | | 2/2014 | Sherman |
| 2014/0276629 A1 | | 9/2014 | Bauer et al. |
| 2015/0065996 A1 | * | 3/2015 | Bartlett, II ............ A61M 1/062 604/514 |

FOREIGN PATENT DOCUMENTS

WO    WO 2014/143130 A1    9/2014

\* cited by examiner

*Primary Examiner* — Nathan R Price
*Assistant Examiner* — Melissa A Snyder
(74) *Attorney, Agent, or Firm* — Kenneth L. Green; Averill & Green

(57) ABSTRACT

A colostrum collection system includes a breast cup, an intermediate reservoir, a syringe attached below the intermediate reservoir, and a vacuum pump drawing vacuum from the breast cup and syringe, through the intermediate reservoir. The vacuum pump maintains vacuum throughout a vacuum pump cycle, but varies the level of the vacuum between a low vacuum and a high vacuum. During high vacuum, the colostrum is drawn from the breast and into the intermediate reservoir, and air is drawn from the syringe creating reduced air pressure in the syringe. During low vacuum, the colostrum is drawn into the syringe by the reduced air pressure in the syringe.

17 Claims, 3 Drawing Sheets

TWO STAGE COLOSTRUM COLLECTION SYSTEM

BACKGROUND OF THE INVENTION

The present invention relates to breast milk collection and in particular to colostrum collection.

Known breast pump systems include vacuum pumps cycling between vacuum and pressure. During vacuum, breast milk is drawn from the breast into an adapter, and the milk flows under gravity from the adapter into a collection bottle attached to the adapter. The breast milk is sufficiently thin to easily flow into the collection bottle. Unfortunately, when known breast pump systems are used to collect thicker colostrum, the systems fail to efficiently draw and deposit the colostrum into the collection bottle.

Further there is a desire to collect colostrum in a syringe for providing the colostrum to a newborn baby. Because it is important to maintain a closed system free of contaminates, it is preferred to directly deliver the colostrum into the syringe through the small passage of the syringe opposite to the piston. Unfortunately, thick colostrum resists flowing through the small passage.

BRIEF SUMMARY OF THE INVENTION

The present invention addresses the above and other needs by providing a colostrum collection system which includes a breast cup, an intermediate reservoir, a syringe attached below the intermediate reservoir, and a vacuum pump drawing vacuum from the breast cup and syringe, through the intermediate reservoir. The vacuum pump maintains vacuum throughout a vacuum pump cycle, but varies the level of the vacuum between a low vacuum and a high vacuum. During high vacuum, the colostrum is drawn from the breast and into the intermediate reservoir, and air is drawn from the syringe creating reduced air pressure in the syringe. During low vacuum, the colostrum is drawn into the syringe by the reduced air pressure in the syringe.

In accordance with one aspect of the invention, there is provided a colostrum collection system maintaining at least a low vacuum at all times. Because colostrum is thicker than breast milk, a system cycling between vacuum and pressure suppresses the flow of colostrum. Maintaining at least low vacuum at all time provides a continuous draw on the colostrum.

In accordance with another aspect of the invention, there is provided a colostrum collection system having unrestricted fluid communication between a collection bottle attached to an intermediate reservoir and vacuum pump. During high vacuum, air is drawn from the collection bottle, during low vacuum, a pressure gradient between the collection bottle and the intermediate reservoir draws colostrum in the intermediate reservoir into the collection bottle.

In accordance with still another aspect of the invention, there is provided a closed colostrum collection system. A filter resides in series with tubing connecting the breast pump to the system preventing ambient air from entering the system and contaminating the colostrum collected by the system.

In accordance with yet another aspect of the invention, there is provided a method for colostrum collection. The method includes connecting a breast pump to an adapter, connecting a breast cup and a reservoir to the adapter, connecting a container to the reservoir, operating the breast pump to provide a cycle of increasing and decreasing vacuum, drawing periodic vacuum from the breast cup, the reservoir, and the container, drawing colostrum from a breast into the reservoir during high vacuum portions of the breast pump period, and drawing the colostrum in the reservoir into the syringe between high vacuum portions of the breast pump period.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement. References to drawing a vacuum are generally equivalent to drawing air from a closed volume.

Figure 1:
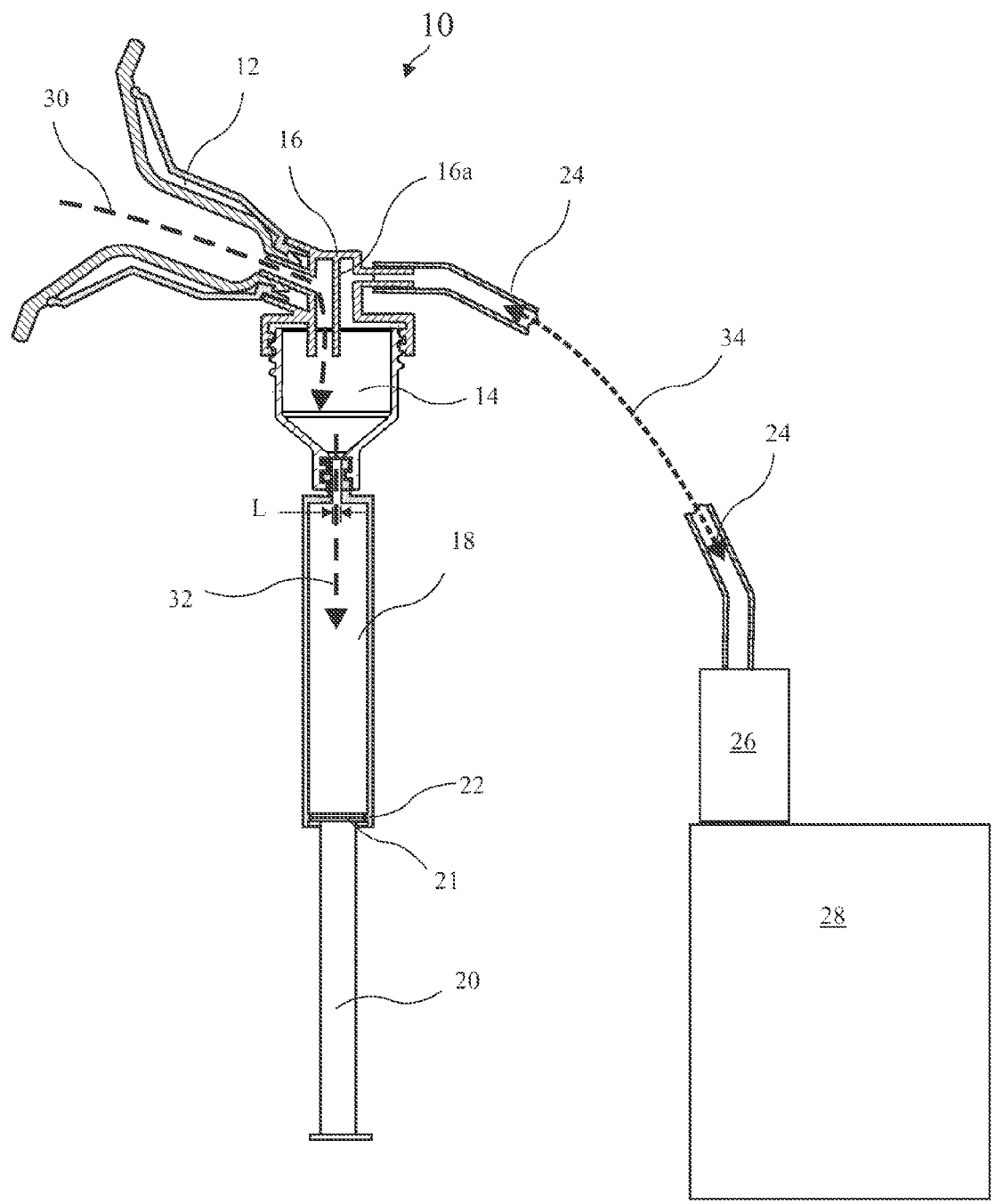
FIG. 1 shows colostrum collection system according to the present invention.

A colostrum collection system 10 according to the present invention is shown in FIG. 1. A breast cup 12 is pressed against a woman's breast and attached to an adapter 16. Tubing 24 connects a breast pump 28 to the adapter 16 to provide fluid communication between the breast pump 28 and the adapter 16. A filter 26 between the breast pump 28 and the adapter 16 prevents contaminants from entering the colostrum collection system 10 which is a closed system. A reservoir 14 is attached to the adapter 16 to collect colostrum received from the breast cup 12 and a container 18 is attached under the reservoir 14. The container 18 is preferably a syringe, and more preferably a syringe including features to retain a syringe piston 20 in a withdrawn position during all of a vacuum cycle of the breast pump 28. The retaining features may be, for example, a raised ring 22 or and annular groove inside the syringe which a piston head 21 engages.

A partition 16a preferably blocks a direct flow from the breast cup 12 into the tubing 24 to deflect colostrum which might otherwise enter the tubing 24. The partition 16a may be a wall, or may be an internal path in the adapter 16, for example, a continuation of the tubing 24. While a separate adapter and reservoir are described in FIG. 1, the adapter and reservoir may be a single piece providing the same function.

The container 18 is preferably a syringe. The syringe has a small luer dimension L of preferably between 2 mm and 4 mm, and more preferably 2.9 mm. Such small luer resists a low of breast milk into the syringe, and even more resists a flow of colostrum into the syringe.

The breast pump 28 provides a vacuum cycle between a minimum vacuum and a maximum vacuum (see FIG. 2) creating an air flow 34 between the breast pump 28 and the adapter 16. The breast pumps 28 preferably maintains vacuum during the entire cycle of breast pump operation, preferably maintaining a minimum vacuum of preferably between 5 millimeters of mercury (mmHg) and 40 mmHg, and more preferably 14 mmHg during the cycle. The breast pump(s) 28 preferably reach a maximum vacuum between 200 mmHg and 400 mmHg, and more preferable around 140 mmHg.

A first flow of colostrum 30 flows from the breast cup 12, through the adapter 16, and into the reservoir 14 while the breast pump in providing higher levels of vacuum, and the flow 30 is reduced or eliminated during lower levels of vacuum. Air is drawn from the container 18 during the higher levels of vacuum creating container vacuum in the container 18. During low levels of vacuum, the container vacuum draws an air flow back into the container 18 through the reservoir, and carries some or all of the colostrum in the reservoir 14 into the container 18 as a second flow of colostrum 32.

Figure 2:
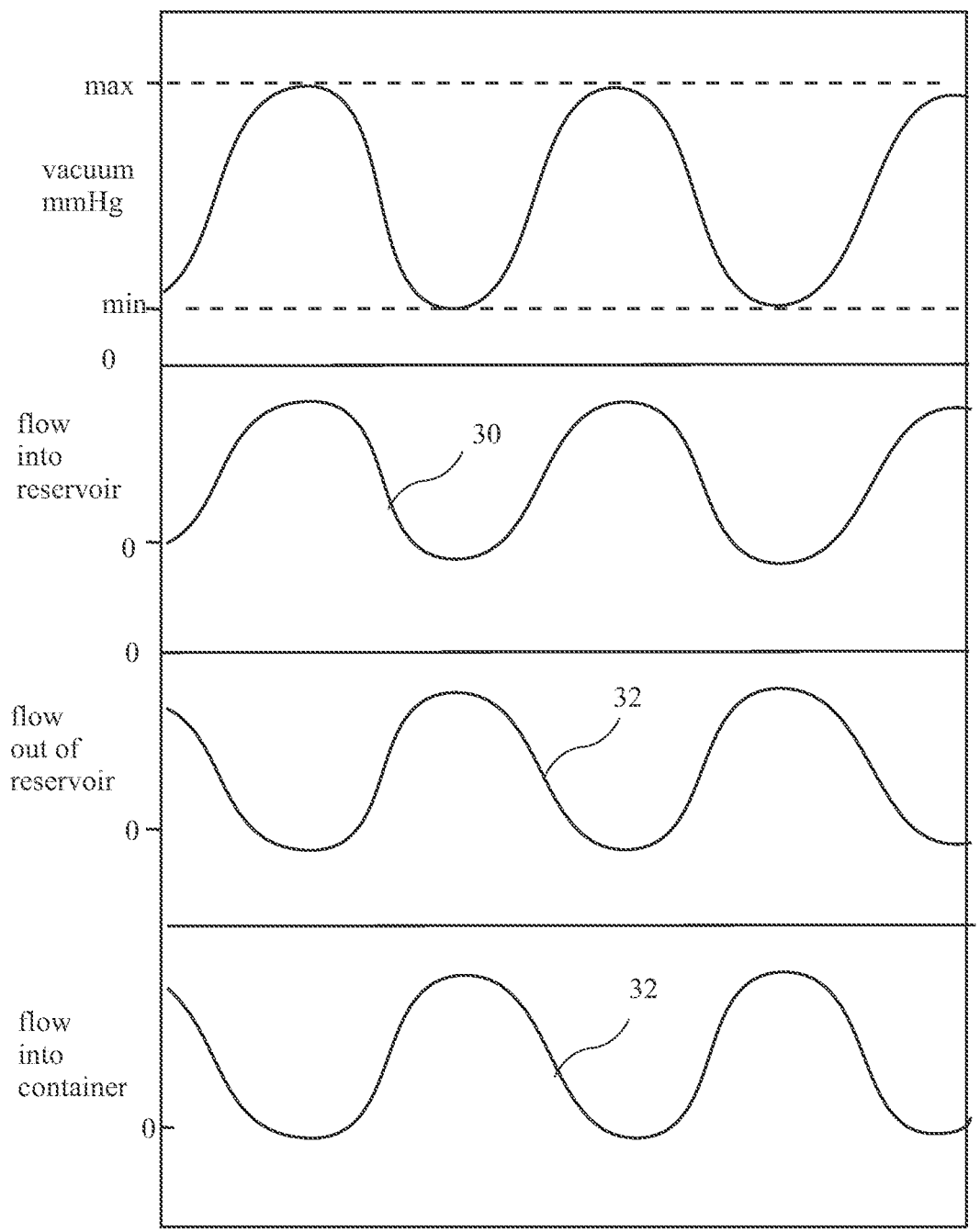
FIG. 2 shows vacuum and flows provided by the present invention.

FIG. 2 shows breast pump vacuum and colostrum flows 30 and 32. The breast pump vacuum is always a positive vacuum (i.e., a negative gauge pressure) between the minimum vacuum and the maximum vacuum. The flow 30 into the reservoir is always positive. The flow 32 represent both a flow from the reservoir and a flow into the container.

Figure 3:
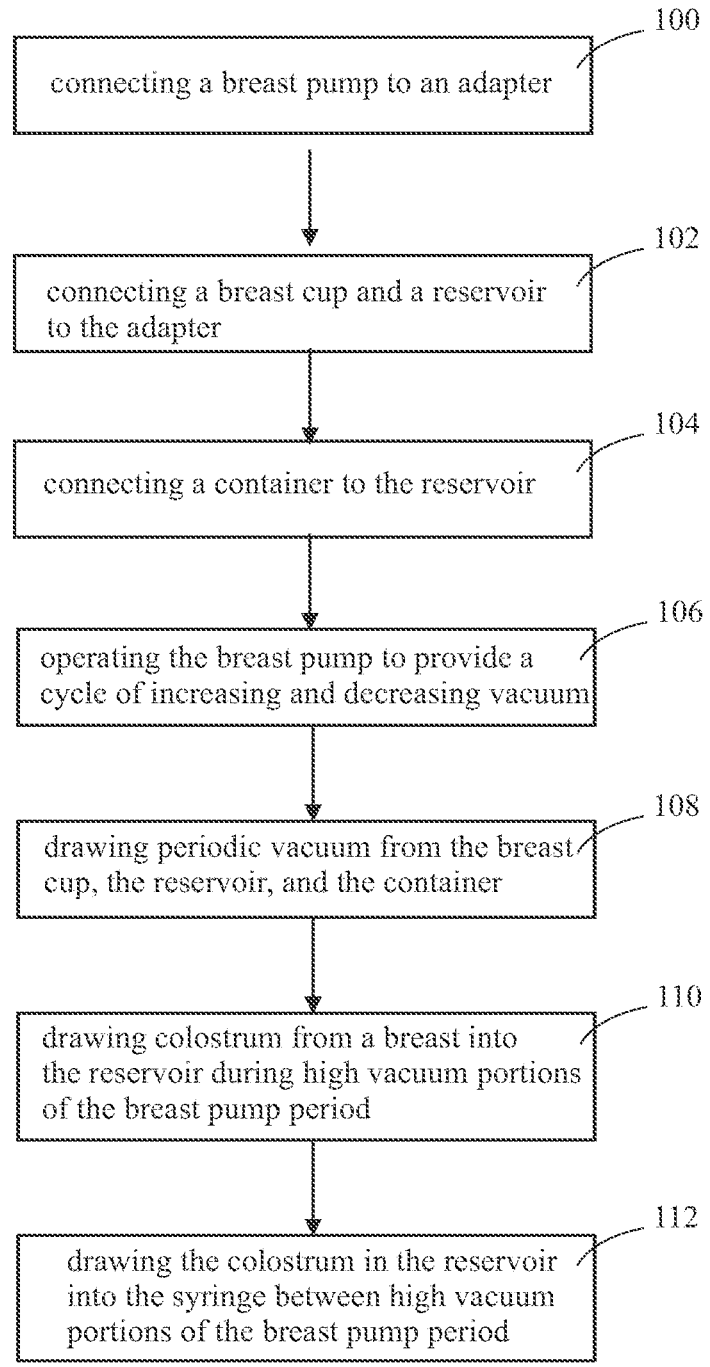
FIG. 3 shows a method according to the present invention.

FIG. 3 shows a method for collecting colostrum according to the present invention. The method includes connecting a breast pump to an adapter at step 100, connecting a breast cup and a reservoir to the adapter at step 102, connecting a container to the reservoir at step 104, operating the breast pump to provide a cycle of increasing and decreasing vacuum at step 106, drawing periodic vacuum from the breast cup, the reservoir, and the container at step 108, drawing colostrum from a breast into the reservoir during high vacuum portions of the breast pump period at step 110, and drawing the colostrum in the reservoir into the syringe between high vacuum portions of the breast pump period at step 112. It is important to note that the flow of colostrum into the reservoir is at high vacuum portions of the cycle, and the flow of colostrum from the reservoir into the container is at low vacuum portions of the cycle, the flow into the container urged by vacuum in the container developing during the high vacuum portions of the cycle.

While the invention herein disclosed has been described by means of specific embodiments and applications thereof, numerous modifications and variations could be made thereto by those skilled in the art without departing from the scope of the invention set forth in the claims.

We claim:

1. A method for collecting colostrum, comprising:
   providing a closed colostrum collection system comprising:
     a breast pump in fluid communication with a reservoir;
     a breast cup in fluid communication with the reservoir;
     a syringe in fluid communication with the reservoir and otherwise closed; and
     a syringe piston in the syringe;
   positioning the syringe piston to engage the syringe in a withdrawn position to provide a fixed syringe volume;
   positioning the breast cup on a breast;
   drawing vacuum from the breast cup, the reservoir, and the syringe, by the breast pump, the vacuum cycling between a minimum vacuum and a maximum vacuum;
   when the vacuum is proximal to the maximum vacuum:
     drawing colostrum from the breast into the reservoir by the vacuum created by the breast pump; and
     drawing air from the syringe creating syringe vacuum in the syringe;
   when the vacuum is proximal to the minimum vacuum:
     releasing the colostrum from the reservoir; and
     drawing the colostrum from the reservoir into the syringe by the syringe vacuum.

2. The method of claim 1, wherein the breast pump is directly connected to an adapter, and the breast cup and the reservoir are in fluid communication with the breast pump through the adapter.

3. The method of claim 1, wherein the syringe is attached to the bottom of the reservoir.

4. The method of claim 1, wherein the syringe includes an interior lip to retain the syringe piston in the withdrawn position.

5. The method of claim 1, wherein positive vacuum is maintained during all operation of the breast pump.

6. The method of claim 5, wherein the positive vacuum is at least 14 mm of mercury (mmHg) during all operation of the breast pump.

7. The method of claim 1, wherein releasing the colostrum from the reservoir into the syringe while the vacuum is proximal the minimum vacuum created by the breast pump is at a portion of the breast pump cycle generally opposite to drawing the colostrum from the breast into the reservoir when the vacuum is proximal to the maximum vacuum.

8. A method for collecting colostrum, comprising:
   providing a closed colostrum collection system comprising:
     a breast pump in fluid communication with an adapter;
     a reservoir in fluid communication with the adapter;
     a breast cup in fluid communication with the adapter; and
     a syringe residing under the reservoir in fluid communication with the reservoir and otherwise closed to fluid communication, the syringe including a raised ring configured to retain a syringe piston in a withdrawn position;
   positioning the syringe piston in the withdrawn position to engage the raised ring to hold the syringe piston in the withdrawn position creating a fixed syringe volume during operation of the breast pump;
   positioning the breast cup on a breast;
   drawing vacuum, through the adapter, from the breast cup, the reservoir, and the syringe, by the breast pump;
   drawing colostrum from the breast through the breast cup and into the adapter while the vacuum is proximal to a maximum vacuum created by the breast pump;
   releasing the colostrum from the adapter into the reservoir;
   creating syringe vacuum in the syringe by drawing air from the syringe when the vacuum created by the breast pump is proximal to the maximum vacuum; and
   drawing the colostrum from the reservoir into the syringe by the syringe vacuum while the vacuum created by the breast pump is less than the maximum vacuum.

9. A method for collecting colostrum, comprising:
   preparing a closed colostrum collection system comprising:
     connecting a vacuum pump in fluid communication to an adapter;
     connecting a breast cup in fluid communication to the adapter;
     connecting a reservoir in fluid communication to the adapter; and connecting a syringe in fluid communication to the reservoir and the syringe otherwise closed to fluid communication;

positioning a syringe piston in a withdrawn position;

retaining the syringe piston in the withdrawn position to provide a fixed syringe volume;

operating the vacuum pump to provide a cycle between a minimum vacuum and a maximum vacuum, the minimum vacuum being at least 14 mmHg;

drawing vacuum from the adapter, the breast cup, and the reservoir, while the vacuum is proximal to the maximum vacuum created by the vacuum pump;

drawing air from the syringe while the vacuum is proximal to the maximum vacuum created by the vacuum pump to create syringe vacuum;

drawing colostrum from the breast into the breast cup while the vacuum is proximal to the maximum vacuum created by the vacuum pump;

passing the colostrum from the breast cup into the adapter and on into the reservoir while the vacuum exceeds the minimum vacuum created by the vacuum pump; and drawing the colostrum from the reservoir into the syringe by the syringe vacuum when the vacuum is proximal to the minimum vacuum created by the vacuum pump.

10. The method of claim 1, wherein syringe has a luer dimension L of between 2 mm and 4 mm and the colostrum is drawn through the luer into the syringe by the syringe vacuum.

11. The method of claim 1, wherein the drawing of the air from the syringe is not restricted.

12. The method of claim 1, wherein:

the breast pump in fluid communication with the reservoir through an adapter;

the breast cup in fluid communication with the reservoir through the adapter; and the reservoir resides under the adapter; and is in fluid communication with the breast pump and the breast cup through the adapter and is in direct fluid communication with the syringe, and is otherwise closed to fluid communication.

13. The method of claim 12, wherein a portion of the adapter providing a path for the colostrum to be released into the reservoir extends down into the reservoir.

14. The method of claim 12, wherein the adapter includes a partition reaching down into the reservoir separating a path for the colostrum from the breast cup into the reservoir from a path for vacuum from the breast pump into the reservoir.

15. The method of claim 1, wherein the syringe and reservoir are in fluid communication with the breast pump and breast cup, but otherwise closed.

16. The method of claim 8, wherein the syringe and reservoir are in fluid communication with the breast pump and breast cup through the adapter, but are otherwise closed.

17. The method of claim 9, wherein the syringe and reservoir are in fluid communication with the breast pump and breast cup through the adapter, but are otherwise closed.

* * * * *